(12) United States Patent
Li et al.

(10) Patent No.: US 11,623,104 B2
(45) Date of Patent: Apr. 11, 2023

(54) PORTABLE INFRARED PHYSIOTHERAPY INSTRUMENT

(71) Applicant: Jiqian Li, Guangzhou (CN)

(72) Inventors: Jiqian Li, Guangzhou (CN); Guangyao Hu, Guangzhou (CN)

(73) Assignee: Jiqian Li, Guangzhou (CN)

( * ) Notice: Subject to any disclaimer, the term of this patent is extended or adjusted under 35 U.S.C. 154(b) by 797 days.

(21) Appl. No.: 16/491,679

(22) PCT Filed: Oct. 27, 2017

(86) PCT No.: PCT/CN2017/108056
§ 371 (c)(1),
(2) Date: Sep. 6, 2019

(87) PCT Pub. No.: WO2019/080102
PCT Pub. Date: May 2, 2019

(65) Prior Publication Data
US 2020/0030630 A1    Jan. 30, 2020

(51) Int. Cl.
*A61N 5/06*    (2006.01)

(52) U.S. Cl.
CPC .... *A61N 5/0625* (2013.01); *A61N 2005/0636* (2013.01); *A61N 2005/0659* (2013.01); *A61N 2005/0662* (2013.01)

(58) Field of Classification Search
CPC .......... A61N 5/0625; A61N 2005/0636; A61N 2005/0659; A61N 2005/0662
See application file for complete search history.

(56) References Cited

U.S. PATENT DOCUMENTS

| 6,290,713 | B1 * | 9/2001 | Russell | A61N 5/0616 |
| | | | | 607/91 |
| 2008/0228247 | A1 * | 9/2008 | Fung | A61H 39/00 |
| | | | | 607/107 |

(Continued)

FOREIGN PATENT DOCUMENTS

| CN | 201443808 U | * | 4/2010 |
| CN | 201443808 U | | 4/2010 |

(Continued)

OTHER PUBLICATIONS

International Search Report, and English Translation thereof, for International Application No. PCT/CN2017/108056, dated May 14, 2018 (6 pages).

(Continued)

*Primary Examiner* — Gary Jackson
*Assistant Examiner* — Sebastian X Lukjan
(74) *Attorney, Agent, or Firm* — Kagan Binder, PLLC

(57) ABSTRACT

Disclosed is a portable infrared physiotherapy instrument (10), comprising a shell (100), a power source (200), a fan (300), an infrared emission assembly (400) and a guide tube (500). The infrared emission assembly (400) comprises a fixing frame (410), and an electric heating wire (420) wound around the fixing frame (410), the electric heating wire (420) being capable of simultaneously generating visible light and heat after being energized, and the heat heating a rare earth coating on the outer surface of the electric heating wire, thereby changing the frequency range of the visible light so as to obtain infrared rays. The power source (200) drives the fan (300) to rotate so as to drive external air to enter the interior of the shell (100) from an opening of a first end of the shell (100) and form an air flow inside the shell (100), and the infrared rays and the heat are guided to the guide tube (500) under the action of the air flow and are discharged from one end of the guide tube (500). The instrument of the (Continued)

present invention is smaller in volume and convenient to carry, and can realize the directional emission of infrared rays and heat and has targeting properties, and the infrared rays and heat simultaneously generated by the electric heating wire (420) can go deep into the skin to perform deep heat therapy, and can effectively improve the effect of physiotherapy.

10 Claims, 6 Drawing Sheets

(56) References Cited

U.S. PATENT DOCUMENTS

| | | | | |
|---|---|---|---|---|
| 2009/0017414 | A1* | 1/2009 | Andersson | A61C 1/08 |
| | | | | 433/29 |
| 2010/0152621 | A1* | 6/2010 | Janna | A61B 5/4504 |
| | | | | 600/595 |
| 2011/0295349 | A1* | 12/2011 | Lin | A61N 5/0619 |
| | | | | 607/103 |
| 2014/0257439 | A1* | 9/2014 | Douglas | A61N 5/0618 |
| | | | | 607/90 |
| 2015/0202458 | A1 | 7/2015 | Angel et al. | |
| 2016/0346162 | A1* | 12/2016 | Powers | A61F 7/007 |

FOREIGN PATENT DOCUMENTS

| | | |
|---|---|---|
| CN | 201528433 U | 7/2010 |
| CN | 202036701 U | 11/2011 |
| CN | 102847236 A | 1/2013 |
| CN | 202722904 U | 2/2013 |

OTHER PUBLICATIONS

Written Opinion for International Application No. PCT/CN2017/108056, dated May 14, 2018 (3 pages).

\* cited by examiner

PORTABLE INFRARED PHYSIOTHERAPY INSTRUMENT

TECHNICAL FIELD

The present disclosure relates to the technical field of physiotherapy instruments, and more particular, to a portable infrared physiotherapy instrument.

BACKGROUND

At present, the common infrared physiotherapy device is mainly composed of a physiotherapy cabin, an infrared emitting element and corresponding auxiliary apparatus, and the infrared emitting element is usually an infrared lamp bead or a lamp tube. By placing a human body in a relatively closed space, and turning on the infrared emitting element to achieve an infrared irradiation to the human body, thereby the physiotherapy effect can be achieved. The infrared physiotherapy device can irradiate surface of the human body in a large area, so that the peripheral nerves and capillaries of the human body are relaxed to a certain extent, and at the same time, it is beneficial to the excretion of the sweat glands of the human epidermis, which has certain physiotherapy effects.

However, the infrared physiotherapy device has a large volume, a heavy weight, a complicated structure, and is not suitable for carrying and transportation. In case of failure, the maintenance cost is high, and the maintenance time is long. Moreover, the body is enclosed in the physiotherapy cabin during performing the physiotherapy, which restricts people's free activities. In the event of a unforeseen safety accident, the patient will be difficult to escape, and the consequences will be disastrous. Secondly, when infrared rays emitted from infrared lamp beads or tubes are used to illuminate the surface of the human body, the heat effect is extremely weak, and the heat effect only acts on the skin surface, and is impossible to penetrate the skin for a heat-therapy. In addition, since the infrared emitting direction of the infrared physiotherapy device is randomly diffused and does not have a targeting property, an accurate physiotherapy to specific parts of the human body cannot be realized.

SUMMARY

Based on this, it is necessary to provide a portable infrared physiotherapy instrument which is small in size, convenient to carry, capable of improving physiotherapy efficacy and has the targeting property, in view of the above technical problems.

A portable infrared physiotherapy instrument including:

a housing, wherein the housing has openings at both ends and is hollow, and the housing includes a first end and a second end that are oppositely disposed.

a power source disposed inside the housing, and configured to supply power;

a fan located inside the housing and corresponding to the first end of the housing, wherein the power source drives the fan to rotate;

an infrared emitting assembly including a fixing mount and a heating wire, wherein the fixing mount is disposed inside the housing, the heating wire is provided to be wound on the fixing mount, and an outer surface of the heating wire is coated with a rare-earth coating, the heating wire can emit a visible light after being energized, and the heat generated by the heating wire after being energized heats the rare-earth coating to change the frequency range of the visible light to form an infrared ray;

a guiding tube, wherein the guiding tube has openings at both ends and is hollow, the guiding tube is disposed on the second end of the housing, and is in communication with the interior of the housing, the infrared emitting assembly is located between the fan and the guiding tube, the heat energy and the infrared ray generated by the heating wire are guided to the guiding tube under the action of the airflow generated by the fan.

In an embodiment, the housing includes a first shell and a second shell that are assembled to form the housing that has openings at both ends and is hollow.

In an embodiment, it further includes a first buckle and a second buckle, both of which are polygonal. The first shell includes a plurality of first sidewalls, and two adjacent first sidewalls are arranged to form an obtuse angle therebetween. The second shell includes a plurality of second sidewalls, and two adjacent second sidewalls are arranged to form an obtuse angle therebetween. One end of the first shell is engaged with one end of the second shell by the first buckle, and the other end of the first shell is engaged with the other end of the second shell by the second buckle.

In an embodiment, the fixing mount includes a plurality of fixing plates that are radially distributed.

In an embodiment, an edge of the fixing plate is provided with a plurality of grooves axially distributed at intervals, and the heating wire is clipped into the groove.

In an embodiment, the heating wire is spiral-shaped, and the number of the heating wires is at least two, and the heating wires are arranged in parallel.

In an embodiment, the infrared emitting assembly further includes a temperature control switch fixed to the fixing mount and electrically connected to the heating wire, and the temperature control switch is configured to switch the power on and power off of the heating wire according to the temperature change.

In an embodiment, it further includes an insulated refractory sleeve that is disposed inside the housing, and is located on an outer side of the infrared emitting assembly, and is in communication with the guiding tube.

In an embodiment, an inner wall of the guiding tube is coated with a coating material having a physiotherapy effect, the guiding tube includes a first guiding tube and a second guiding tube, the first guiding tube is adjacent to the second end of the housing, and the inner diameter of the first guiding tube is smaller than the inner diameter of the second guiding tube.

In an embodiment, it further includes a heat dissipating tube that is sleeved on the outside of the guiding tube, and the sidewall of the heat dissipating tube is provided with a heat dissipating hole.

The above portable infrared physiotherapy instrument has at least the following advantages.

The heating wire can generate the visible light and the heat simultaneously after being energized, and the heat heats the rare-earth coating on the outer surface of the heating wire, thereby changing the frequency range of visible light to obtain the infrared ray. The power source drives the fan to rotate, which may cause the outside air enters the interior of the housing via the opening of the first end of the housing, thereby an airflow may be formed inside the housing. The infrared ray and the heat energy may be guided to the guiding tube under the action of the airflow, and may be discharged from one end of the guiding tube. The above portable infrared physiotherapy instrument is not only small in size and convenient to carry, but also capable of realizing the directional emission of the infrared ray and heat energy, and has the targeting property. The infrared ray and heat energy generated simultaneously by the heating wire can penetrate the skin to perform the deep heat-therapy, which can effectively improve the physiotherapy effect.

DETAILED DESCRIPTION OF THE EMBODIMENTS

Reference will be made to the drawings to describe embodiments of the present disclosure in detail, so that the above objects, features and advantages of the present disclosure can be more apparent and understandable. In the following description, numerous specific details are set forth in order to provide a thorough understanding of the present disclosure. However, the present disclosure can be implemented in many other ways which are different from those described herein, and those skilled in the art can make similar improvements without departing from the essence of the present disclosure. Therefore, the present disclosure is not limited by the specific embodiments disclosed below.

It should be understood that when an element is defined as "fixed to" another element, it is either directly on an element or indirectly on an element with a mediating element. When an element is considered to be "connected to" another element, it can be directly connected to another element or indirectly connected to another element with a mediating element. The terms "vertical", "horizontal", "left", "right", and the like used herein are for illustrative purposes only and are not intended to be the only embodiment.

All technical and scientific terms used herein have the same meaning as commonly understood by one skilled in the art, unless otherwise defined. The terms used herein are for the purpose of describing specific embodiments only and are not intended to limit the present disclosure. Each of the technical features of the above-described embodiments may be combined arbitrarily. To simplify the description, not all the possible combinations of each of the technical features in the above embodiments are described. However, all of the combinations of these technical features should be considered as within the scope of the present specification, as long as such combinations do not contradict with each other.

Figure 1:
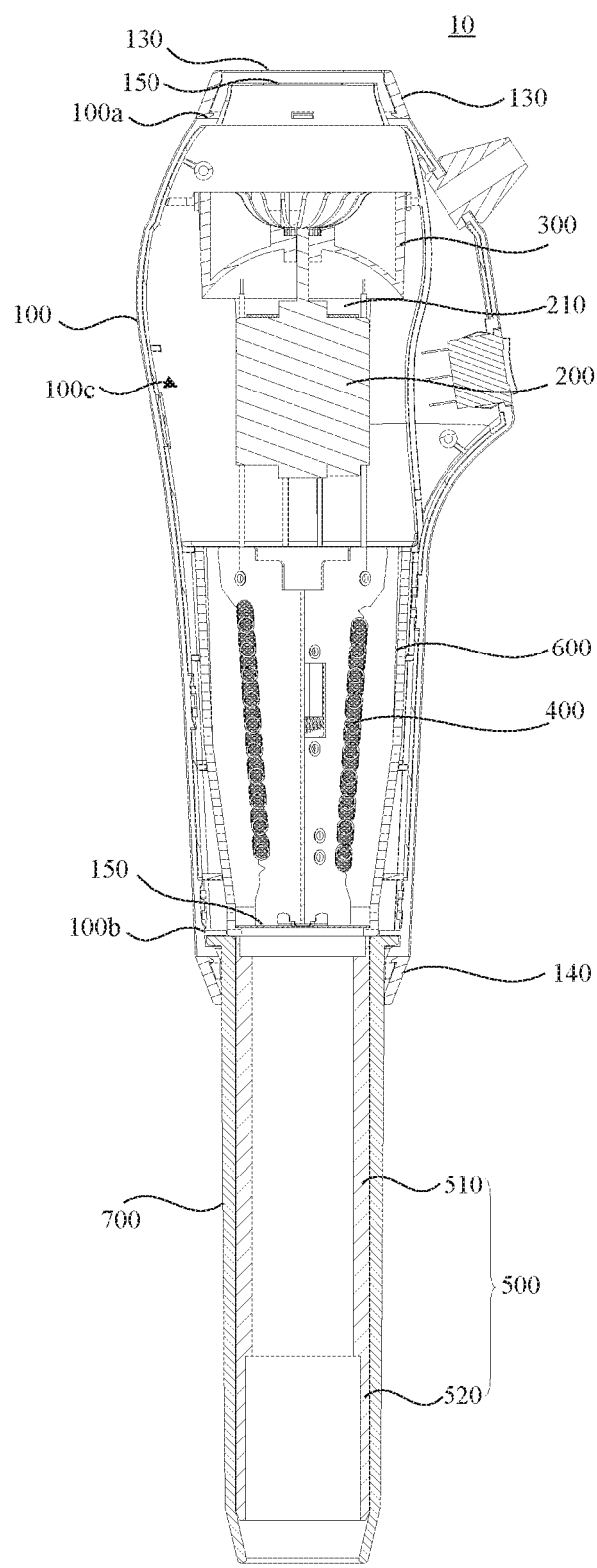
FIG. 1 is a cross sectional diagram of a portable infrared physiotherapy instrument in an embodiment.
Figure 2:
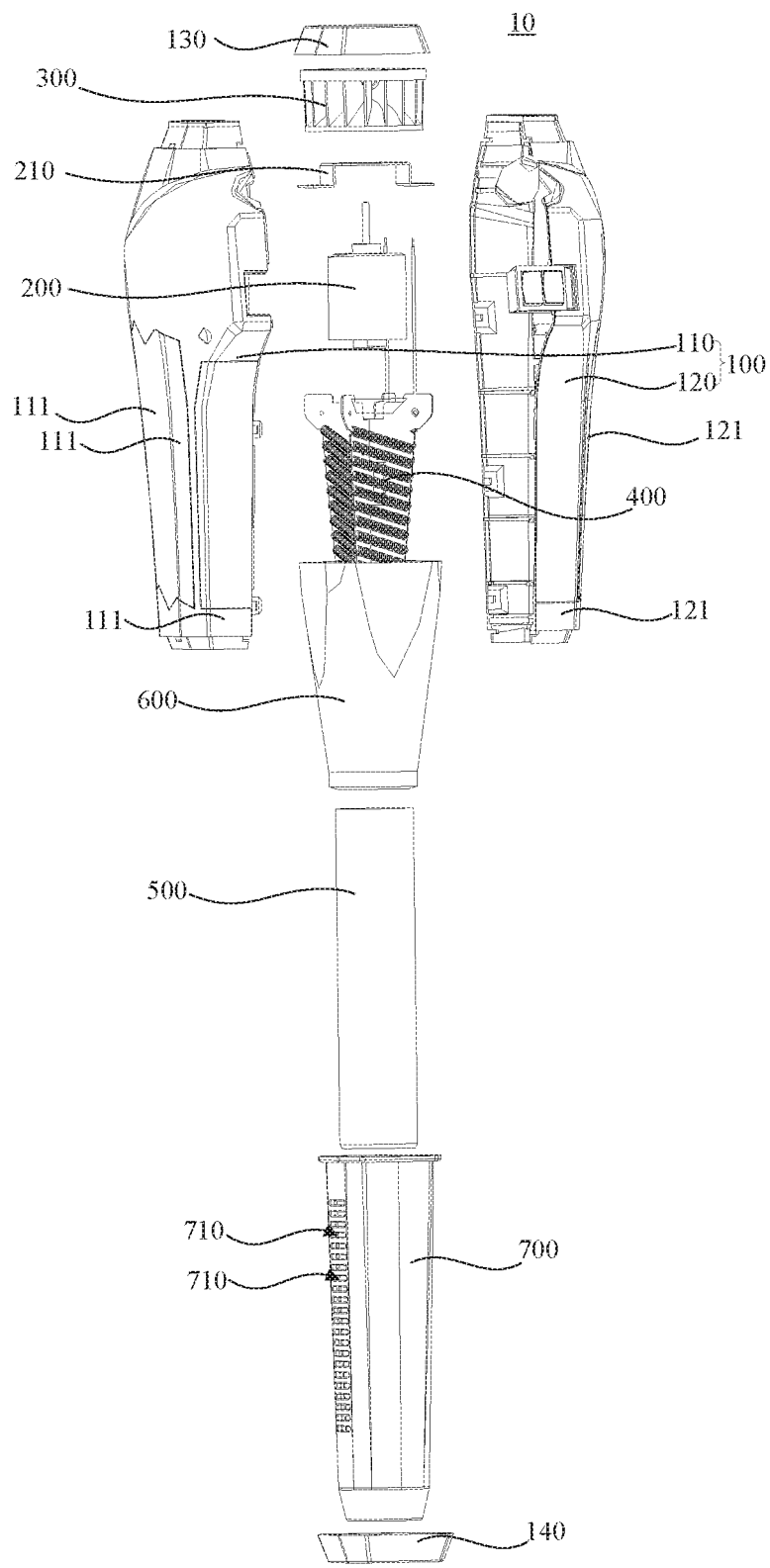
FIG. 2 is an exploded perspective diagram of the portable infrared physiotherapy instrument of FIG. 1.
Figure 3:
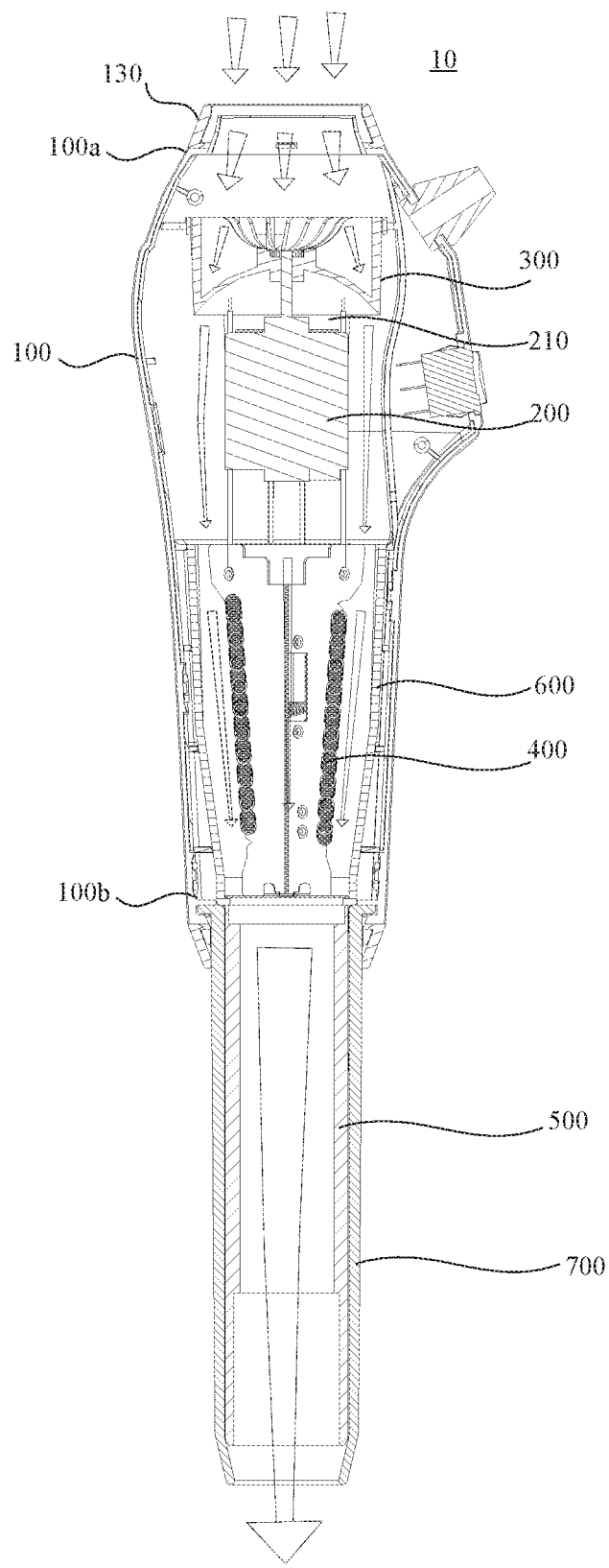
FIG. 3 is a schematic diagram illustrating an airflow guiding of the portable infrared physiotherapy instrument of FIG. 1.

Referring to FIGS. 1-3, a portable infrared physiotherapy instrument 10 in an embodiment is not only small in size and convenient to carry, but also capable of improving the physiotherapy effect, and the infrared physiotherapy performed by the portable infrared physiotherapy instrument 10 has the targeting property, which is capable of realizing the directional emission to specific parts of the patient. Specifically, the portable infrared physiotherapy instrument 10 includes a housing 100, a power source 200, a fan 300, an infrared emitting assembly 400, a guiding tube 500, an insulated refractory sleeve 600, and a heat dissipating tube 700.

The housing 100 has openings at both ends and is hollow. A receiving cavity 100c is formed inside the housing 100 and is configured to accommodate components and parts such as the power source 200, the fan 300, the infrared emitting assembly 400, and the insulated refractory sleeve 600, and the like. The housing 100 includes a first end 100a and a second end 100b that that are oppositely disposed. An opening corresponding to the first end 100a is provided with a filter screen 150, and an opening corresponding to the second end 100b is also provided with the filter screen 150.

The housing 100 includes a first shell 110 and a second shell 120 that are assembled to form the hollow housing 100 that has openings at both ends and is hollow. Specifically, the first shell 110 includes a plurality of first sidewalls 111, and two adjacent first sidewalls 111 are arranged to form an obtuse angle therebetween. The second shell 120 includes a plurality of second sidewalls 121, and two adjacent second sidewalls 121 are arranged to form an obtuse angle therebetween. One end of the first shell 110 is engaged with one end of the second shell 120 by a first buckle 130 that is polygonal. The other end of the first shell 110 is engaged with the other end of the second shell 120 by a second buckle 140 that is also polygonal. Therefore, the first shell 110 and the second shell 120 are engaged by the first buckle 130 and the second buckle 140, which saves time and labor compared with the manner of fixing by a plurality of screws.

The power source 200 is disposed inside the housing 100, and is configured to provide power, and is fixed to the inner wall of the housing 100 by a rack. Specifically, the power source 200 can be an electric motor. The electric motor is fixed to the sidewall of the housing 100 by a rack 210. For example, a fixing rib may be formed on the inner wall of the housing 100, the rack 210 is fixed to the fixing rib, and the electric motor is fixed to the rack 210.

The fan 300 is located inside the housing 100, and is corresponding to the first end 100a of the housing 100, and is driven to rotate by the power source 200. Specifically, the fan 300 is disposed on an output end of the electric motor, and is driven to rotate by the output end when the electric motor is in operation. The fan 300 may be an axial fan that faces the opening of the first end 100a. When the fan 300 rotates, outside air enters the inside of the housing 100 via the opening of the first end 100a, and forms an airflow under the action of the fan 300, and the flow direction of the airflow is indicated by the direction of the broken arrow in FIG. 3. When using the axial fan, the overall space size of the housing 100 can be effectively reduced. Certainly, in other embodiments, the fan 300 can also employ a centrifugal fan.

Figure 4:
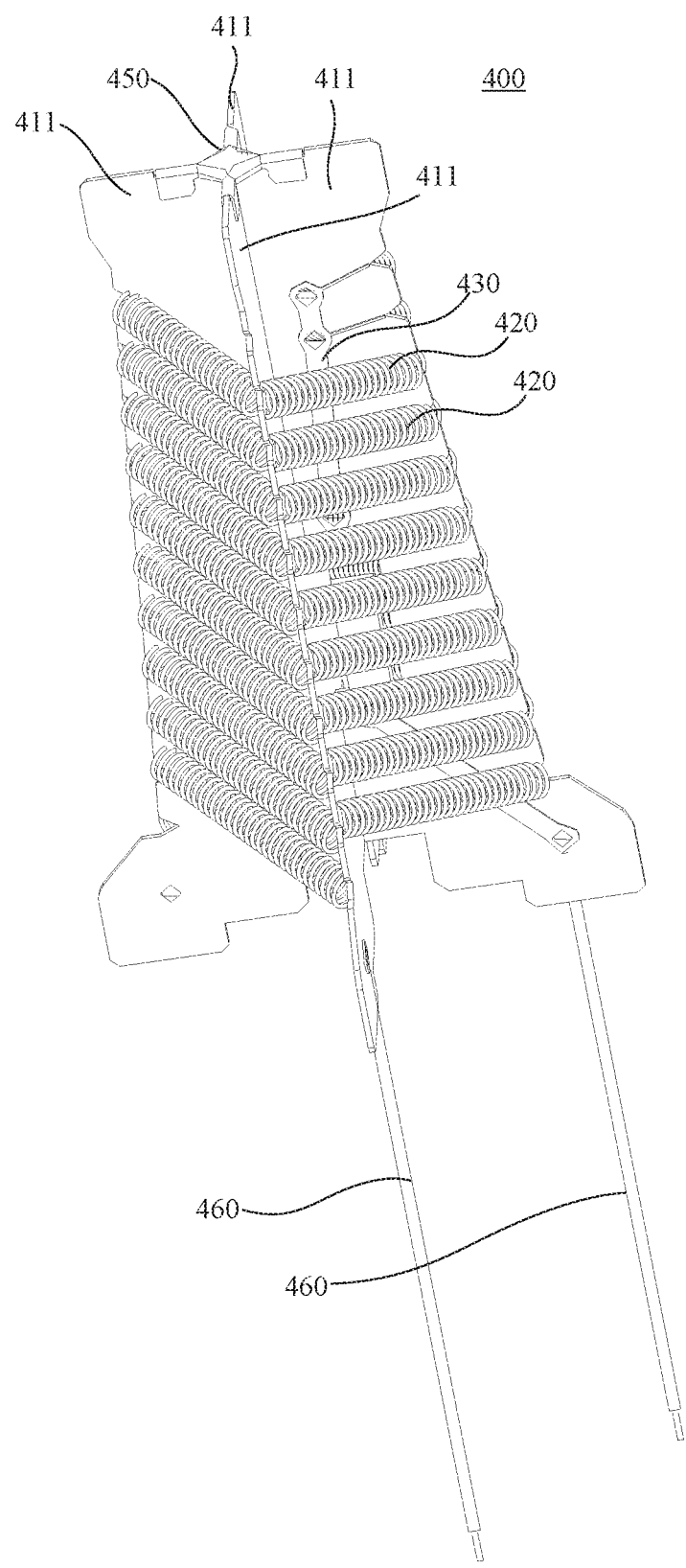
FIG. 4 is a schematic structural diagram of an infrared emitting assembly of FIG. 2.
Figure 5:
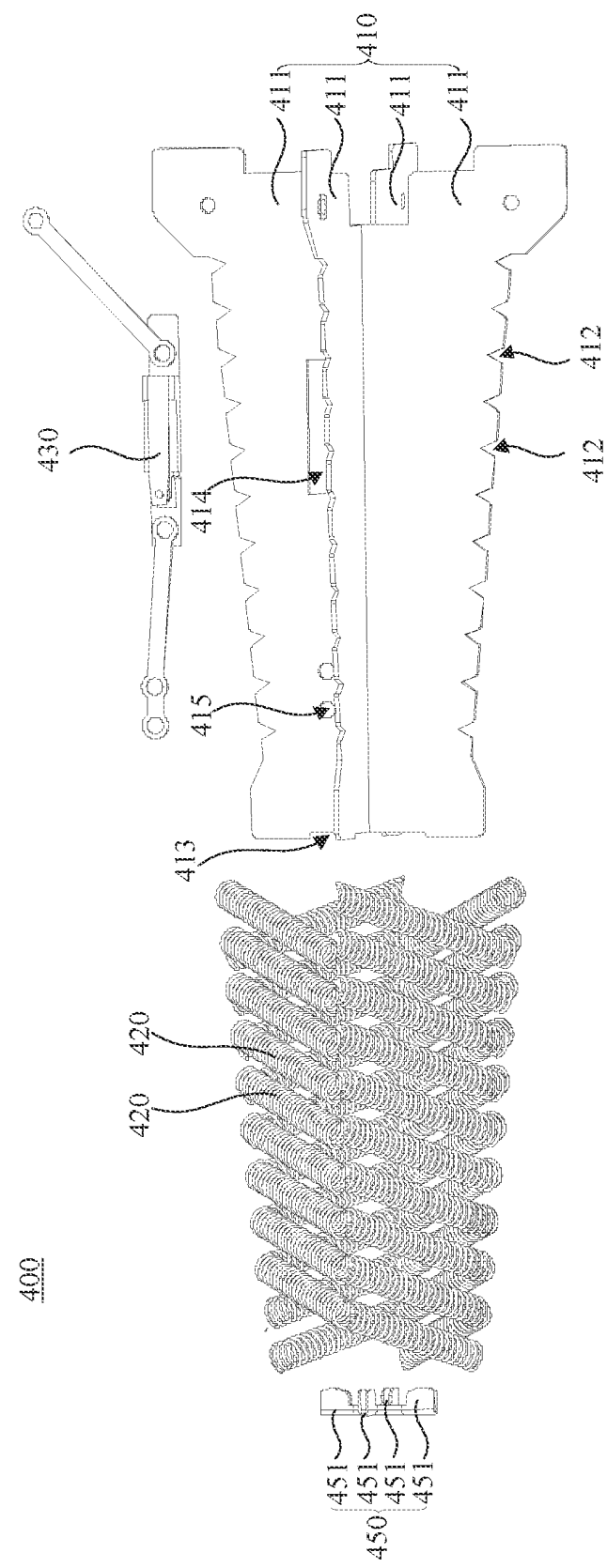
FIG. 5 is a schematic exploded diagram of the infrared emitting assembly of FIG. 4.

Referring to FIG. 4 and FIG. 5 together, the infrared emitting assembly 400 includes a fixing mount 410 disposed inside the housing 100, a heating wire 420 provided to be wound on the fixing mount 410 and a temperature control switch 430. An outer surface of the heating wire 420 is coated with a rare-earth coating, the heating wire can emit the visible light after being energized, and the heat generated by the heating wire after being energized heats the rare-earth coating to change the frequency range of the visible light to form the infrared ray. Specifically, the wavelength of the infrared ray ranges from 3 μm to 30 μm.

Specifically, the fixing mount 410 includes a plurality of fixing plates 411 that are radially distributed. For example, the number of the fixing plates 411 is four, and the two adjacent fixing plates 411 are arranged at right angles to form the fixing mount 410 with a cross-shaped cross section. The "right angle" may allow a certain manufacturing or assembly error as long as it satisfies the requirements. Therefore, when the airflow formed when the fan 300 rotates flows through the fixing mount 410, since the fixing mount 410 has a small blocking effect on the airflow, it is more advantageous for the airflow to flow through the infrared emitting assembly 400.

Certainly, in other embodiments, the number of the fixing plates 411 may be other numbers, and is not specifically limited. Certainly, in other embodiments, the fixing mount 410 may be other shapes, and is not limited to the shape composed of a plurality of fixing plates 411.

Specifically, in the present embodiment, the edge of the fixing plate 411 is provided with a plurality of grooves 412 into which the heating wire 420 is clipped, so that firmness between the heating wire 420 and the fixing mount 410 can be increased. The plurality of grooves 412 are arranged at intervals along an axial direction of the fixing mount 410. For example, the heating wire 420 is wound five turns, and therefore, the number of corresponding grooves 412 on the fixing plate 411 is also five.

The radial width of a part of the fixing plate 411 for being wound by the heating wire 420 gradually increases along the axial direction. Specifically, the end of the part of the fixing plate 411 for being wound by the heating wire 420 adjacent to the fan 300 has a radial width greater than the radial width of the end of the same part away from the fan 300. Therefore, when the heating wire 420 is wound on the fixing plate 411, the radial sizes of the heating wires 420 corresponding to the different grooves 412 are different, which facilitates to increase the contact area between the heating wire 420 and the airflow, and is more advantageous for the airflow to direct the infrared ray and the heat energy generated by the heating wire 420 to the guiding tube 500.

The temperature control switch 430 is fixed on the fixing mount 410, and is electrically connected to the heating wire 420, and is configured to switch the power on and power off of the heating wire 420 according to the temperature change. Specifically, the fixing plate 411 is provided with an opening 414, and a main body portion of the temperature control switch 430 is fixed on the opening 414. The fixing plate 411 is further provided with a through hole 415, and a connection terminal of the temperature control switch 430 is located on the through hole 415.

Specifically, in the present embodiment, the heating wire 420 is spiral-shaped, and both ends of the heating wire 420 are electrically connected to the power source via conductive wires 460 respectively. Specifically, the number of the heating wires 420 is two, and both two heating wires 420 are spiral-shaped and wound on the fixing mount 410 respectively. Two heating wires 420 are arranged in parallel. For example, the two heating wires 420 are rated at 1200 W. Certainly, in other embodiments, the number of heating wires 420 can be selected according to actual needs.

When the heating wire 420 is wound on the fixing mount 410, the heating wire 420 itself is spiral-shaped and then spirally wound on the outer circumference of the fixing mount 410. Since the side of the fixing plate 411 is provided with the groove 412, when the heating wire 420 is in contact with the fixing plate 411, the heating wire 420 is clipped into the groove 412, so that the connection between the heating wire 420 and the fixing mount 410 is more secure.

The infrared emitting assembly 400 further includes a frame fixing buckle 450 disposed at the end of the fixing mount 410. The frame fixing buckle 450 includes a plurality of latching portions 451 that are radially distributed. The number of the latching portions 451 is the same as the number of the fixing plates 411, and the latching portions 451 are snapped to the end of the fixing plates 411. For example, in the present embodiment, the cross section of the frame fixing buckle 450 is also cross-shaped, and the frame fixing buckle 450 includes four latching portions 451. The four latching portions 451 are respectively snapped to the ends of the four fixing plates 411.

Specifically, in the present embodiment, a receiving groove 413 may also be formed in the end of the fixing plate 411. When the latching portion 451 is snapped to the end of the fixing plate 411, the latching portion 451 is located in the receiving groove 413. Therefore, the size of portion of the frame fixing buckle 450 protruding from the end of the fixing plate 411 can be reduced, which causes a more reasonable spatial structure setting. The frame fixing buckle 450 is located on the second end 100*b* of the housing 100 and is disposed corresponding to one end of the guiding tube 500.

Specifically, in the present embodiment, the portable infrared physiotherapy instrument 10 further includes an insulated refractory sleeve 600 disposed inside the housing 100. For example, a plurality of reinforcing ribs radially distributed at intervals are formed on the inner sidewall of the housing 100, and each reinforcing rib extends radially, and the outer sidewall of the insulated refractory sleeve 600 abuts against the reinforcing ribs to prevent the insulated refractory sleeve 600 and the housing 100 form moving relative to each other. The insulated refractory sleeve 600 is sleeved on the outside of the infrared emitting assembly 400, and is in communication with the guiding tube 500.

Specifically, the insulated refractory sleeve 600 has a tubular structure with a large end and a small end, and the fixing mount 410 is received inside the insulated refractory sleeve 600. The insulated refractory sleeve 600 is configured with the large end facing the fan 300 and the small end facing the guiding tube 500. Specifically, a filter screen may be provided on the small end of the insulated refractory sleeve 600 for preventing the components and parts inside the housing 100 from entering the guiding tube 500 to block the guiding tube 500.

Figure 6:
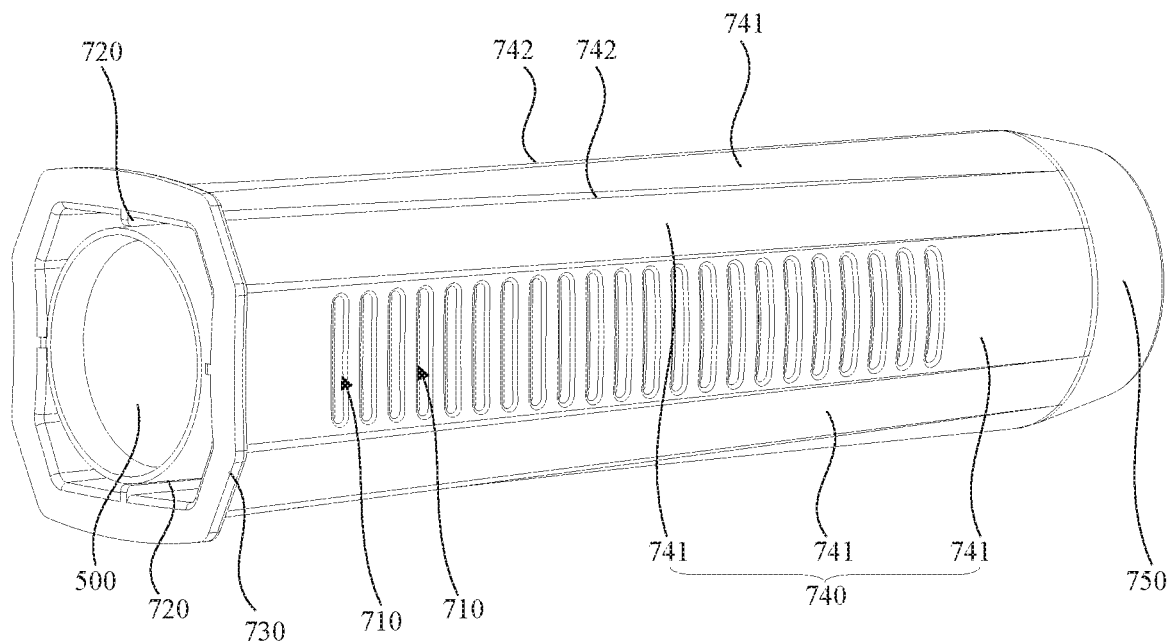
FIG. 6 is a schematic diagram illustrating the assembly of a guiding tube and a heat dissipating tube of FIG. 2.
Figure 7:
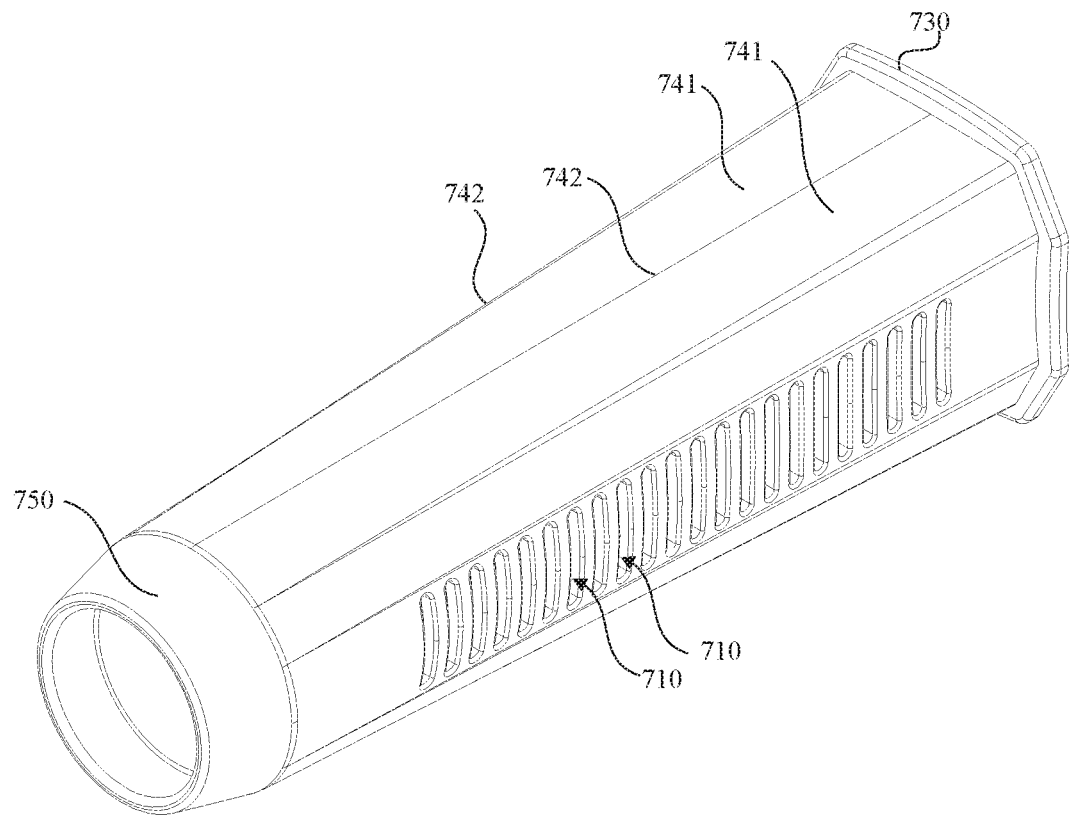
FIG. 7 is a schematic diagram illustrating the assembly of a guiding tube and a heat dissipating tube of FIG. 6 from another angle of view.

Referring to FIG. 6 and FIG. 7 together, the guiding tube 500 is disposed on one end of the housing 100, and the infrared emitting assembly 400 is located between the fan 300 and the guiding tube 500. Specifically, the guiding tube 500 is a hollow tubular structure with openings at both ends, and is located on the second end 100*b* of the housing 100. The airflow generated by the rotation of the fan 300 flows along the direction from the first end 100*a* to the second end 100*b*. The heat energy and the infrared ray generated by the infrared emitting assembly 400 are guided to the guiding tube 500 under the action of the airflow generated by the fan 300, and then are discharged via the guiding tube 500, which realizes the purpose of directional emission of the infrared ray and the heat energy.

The inner wall of the guiding tube 500 is coated with the coating material having a physiotherapy effect, so that when the heat energy and the infrared ray are discharged via the guiding tube 500, negative ions and nano-silver ions released from the physiotherapy coating material on the inner wall of the guiding tube 500 are also led out along with the airflow. The guiding tube 500 includes a first guiding tube 510 and a second guiding tube 520. The first guiding tube 510 is adjacent to the second end 100b of the housing 100 and the inner diameter of the first guiding tube 510 is smaller than the inner diameter of the second guiding tube 520.

Specifically, both the first guiding tube 510 and the second guiding tube 520 are metal heat dissipating tube which has great heat conductivity and can achieve high-efficiency heat dissipation. Therefore, the first guiding tube 510 and the second guiding tube 520 have both a guiding function and a heat dissipation function. Certainly, in other embodiments, the first guiding tube 510 and the second guiding tube 520 can also be made of other materials with great heat dissipation performance.

The first guiding tube 510 and the second guiding tube 520 have the same outer diameter, and are formed integrally, the first guiding tube 510 is located on one end of the second guiding tube 520, and the first guiding tube 510 is located on the end adjacent to the infrared emitting assembly 400, and the second guiding tube 520 is located on the end away from the infrared emitting assembly 400. The length of the first guiding tube 510 is greater than the length of the second guiding tube 520.

Specifically, in the embodiment, the portable infrared physiotherapy instrument 10 further includes a heat dissipating tube 700 that is sleeved on the outside of the guiding tube 500. The heat dissipating tube 700 is provided with a heat dissipating hole 710 for dissipating heat by means of air heat dissipation. The heat dissipating tube 700 conducts heat energy of the guiding tube 500 to outside air.

The number of the heat dissipating holes 710 is plural, and the plurality of heat dissipation holes 710 are arranged at intervals along the axial direction of the heat dissipating tube 700, and each heat dissipating hole 710 extends along the radial direction of the heat dissipating tube 700. When the heat energy and the infrared ray generated by the infrared emitting assembly 400 are guided to the guiding tube 500 under the action of the airflow generated when the fan 300 rotates, the guiding tube 500 not only has a guiding effect but also contacts the heat energy to dissipate heat. The heat dissipating tube 700 is in contact with the guiding tube 500, thus the heat energy can be further dissipated via the heat dissipating tube 700. The heat dissipating tube 700 is provided with the heat dissipation hole 710, and the heat energy corresponding to the heat dissipating hole 710 is directly in contact with the air to achieve a heat dissipation effect.

The inner wall of the heat dissipating tube 700 is further provided with a positioning rib 720 for preventing the guiding tube 500 and the heat dissipating tube 700 from moving relative to each other. Specifically, there are a plurality of the positioning ribs 720 that are radially distributed at intervals on the inner wall of the heat dissipating tube 700, and each positioning ribs 720 extends along the axial direction of the heat dissipating tube 700.

The heat dissipating tube 700 includes a fixing portion 730, a heat dissipating portion 740, and a guiding portion 750. The heat dissipating portion 740 is located between the fixing portion 730 and the guiding portion 750. The fixing portion 730 is configured to fix to the housing 100, and the heat dissipating portion 740 is configured to dissipate heat. The heat dissipating hole 710 is provided on the heat dissipating portion 740. The diameter of the guiding portion 750 gradually decreases along the direction away from the fixing portion 730, so that the infrared rays tend to gradually gather when they are led out.

The heat dissipating portion 740 includes a plurality of third sidewalls 741 that are connected end to end to form the tubular structure that has openings at both ends and a hollow interior. The tubular structure has a plurality of ridgelines 742 parallel to each other. The shape of the cross section of the fixing portion 730 is substantially the same as the shape of the cross section of the heat dissipating portion 740. Therefore, when the fixing portion 730 and the housing 100 are fixed to each other, they can be directly engaged by the second buckle 140 having the similar shape of the cross section, which achieves a convenient, fast and reliable fixation.

Specifically, in the present embodiment, the fixing plate 411 is further provided with a light board that is electrically connected with an indicator light. For example, four blue light beads are provided on the light board by welding. When the heating wire is energized and operating, the four blue light beads are lit, and the emitted blue light is emitted from the guiding tube, which indicates the direction of the airflow.

The above portable infrared physiotherapy instrument 10 has at least the following advantages.

The heating wire 420 can generate the visible light and the heat simultaneously after being energized, and the heat heats the rare-earth coating on the outer surface of the heating wire, thereby changing the frequency range of visible light to obtain the infrared ray. The power source 200 drives the fan 300 to rotate, which may cause the outside air enters the interior of the housing 100 via the opening of the first end 100a of the housing 100, thereby an airflow may be formed inside the housing 100. The infrared ray and the heat energy may be guided to the guiding tube 500 under the action of the airflow, and may be discharged from one end of the guiding tube 500. The above portable infrared physiotherapy instrument is not only small in size and convenient to carry, but also capable of realizing the directional emission of the infrared ray and heat energy, and has the targeting property. The infrared ray and heat energy generated simultaneously by the heating wire 420 can penetrate the skin to perform the deep heat-therapy, which can effectively improve the physiotherapy effect.

The above-described embodiments merely represent several embodiments of the present disclosure, and the description thereof is more specific and detailed, but it should not be construed as limiting the scope of the present disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

What is claimed is:

1. A portable infrared physiotherapy instrument, comprising:
   a housing, wherein the housing has openings at both ends and is hollow, and the housing includes a first end and a second end that are oppositely disposed.
   a power source disposed inside the housing, and configured to supply power;
   a fan located inside the housing and corresponding to the first end of the housing, wherein the power source drives the fan to rotate;
   an infrared emitting assembly including a fixing mount and a heating wire, wherein the fixing mount 1 s disposed inside the housing, the heating wire is provided to be wound on the fixing mount, and an outer surface of the heating wire is coated with a rare-earth coating, the heating wire emits visible light after being energized, and heat generated by the heating wire after being energized heats the rare-earth coating to change the frequency range of the visible light to form the infrared ray; and a guiding tube, wherein the guiding tube has openings at both ends and is hollow, the guiding tube is disposed on the second end of the housing, and is in communication with the interior of the housing, the infrared emitting assembly is located between the fan and the guiding tube, the heat energy and the infrared ray generated by the heating wire are guided to the guiding tube under the action of the airflow generated by the fan, wherein the inner wall of the guiding tube is coated with a coating material having a physiotherapy effect when the heat energy and the infrared ray are discharged via the guiding tube and negative ions and nano-silver ions are released from the coating material on the inner wall of the guiding tube and are led out along with airflow.

2. The portable infrared physiotherapy instrument of claim 1, wherein the housing includes a first shell and a second shell that are assembled to form the housing that has openings at both ends and is hollow.

3. The portable infrared physiotherapy instrument of claim 2, wherein it further comprises a first buckle and a second buckle, both of which are polygonal, the first shell includes a plurality of first sidewalls, and two adjacent first sidewalls are arranged to form an obtuse angle therebetween, the second shell includes a plurality of second sidewalls, and two adjacent second sidewalls are arranged to form an obtuse angle therebetween, one end of the first shell is engaged with one end of the second shell by the first buckle, and the other end of the first shell is engaged with the other end of the second shell by the second buckle.

4. The portable infrared physiotherapy instrument of claim 1, wherein the fixing mount includes a plurality of fixing plates that are radially distributed.

5. The portable infrared physiotherapy instrument of claim 4, wherein an edge of each of the fixing plates is provided with a plurality of grooves axially distributed at intervals, and the heating wire is clipped into the groove.

6. The portable infrared physiotherapy instrument of claim 1, wherein the heating wire is spiral-shaped, and the number of the heating wires is at least two, and the heating wires are arranged in parallel.

7. The portable infrared physiotherapy instrument of claim 1, wherein the infrared emitting assembly further includes a temperature control switch that is fixed to the fixing mount, and is electrically connected to the heating wire, and is configured to switch the power on and power off of the heating wire according to a temperature change.

8. The portable infrared physiotherapy instrument of claim 1, wherein it further comprises an insulated refractory sleeve that is disposed inside the housing, is located on an outer side of the infrared emitting assembly, and is in communication with the guiding tube.

9. The portable infrared physiotherapy instrument of claim 1, wherein the guiding tube includes a first guiding tube and a second guiding tube, the first guiding tube is adjacent to the second end of the housing, and the inner diameter of the first guiding tube is smaller than the inner diameter of the second guiding tube.

10. The portable infrared physiotherapy instrument of claim 1, wherein it further comprises a heat dissipating tube that is sleeved on the outside of the guiding tube, and sidewall of the heat dissipating tube is provided with a heat dissipating hole.

* * * * *